United States Patent
Silver et al.

(10) Patent No.: US 6,466,638 B1
(45) Date of Patent: Oct. 15, 2002

(54) IMAGE MAPPING METHOD AND SYSTEM

(75) Inventors: Michael D. Silver, Northbrook; Anindya Sen, Vernon Hills, both of IL (US)

(73) Assignee: Kabushiki Kaisha Toshiba, Kawasaki (JP)

( * ) Notice: Subject to any disclaimer, the term of this patent is extended or adjusted under 35 U.S.C. 154(b) by 0 days.

(21) Appl. No.: 09/502,451

(22) Filed: Feb. 11, 2000

(51) Int. Cl.⁷ .................................................. A61B 6/03
(52) U.S. Cl. ............................................ 378/4; 378/901
(58) Field of Search ............................ 378/4, 15, 17, 378/901

(56) References Cited

U.S. PATENT DOCUMENTS

| | | | | |
|---|---|---|---|---|
| 5,963,612 A | * | 10/1999 | Navab | 378/4 |
| 5,963,613 A | * | 10/1999 | Navab | 378/4 |
| 6,044,132 A | * | 3/2000 | Navab | 378/163 |
| 6,049,582 A | * | 4/2000 | Navab | 378/4 |

* cited by examiner

Primary Examiner—David V. Bruce
(74) Attorney, Agent, or Firm—Oblon, Spivak, McClelland, Maier & Neustadt, P.C.

(57) ABSTRACT

A method and system for reconstructing an x-ray image through mapping. The system rotates an x-ray source and an x-ray detector in an irregular path. A calibration factor matrix for each position of a source and detector is calculated using a calibration phantom and then stored for use during reconstruction. The image is reconstructed by mapping a reprojected image point from a known coordinate using the calibration factors. The mapping takes into consideration the non-idealities in the irregular path, improving the image reconstruction.

18 Claims, 8 Drawing Sheets

IMAGE MAPPING METHOD AND SYSTEM

BACKGROUND OF THE INVENTION

1. Field of the Invention

The present invention relates to a method and system for image reconstruction in cone-beam X-ray computed tomography and, in particular, to a method and system using mapping coefficients to reconstruct the image.

2. Discussion of the Background

Cone beam computed tomography (CT) reconstructs the interior of an object or It( patient from the two-dimensional projections of transmitted x-rays through the object or patient. Feldkamp, Kress, and Davis introduced an approximate but computationally efficient image reconstruction algorithm, termed convolution backprojection, for the case of a circular orbit of the X-ray source around an object or patient. The algorithm assumes that the rotational axis is fixed and that the mid-plane of the x-rays is fixed.

In recent years, there has been an attempt to implement cone-beam CT on C-arm gantries that only revolve around a portion of the object or patient during imaging. In medical CT, C-arm gantries are desirable because they provide some access to a patient for simultaneous intervention by medical personnel. Furthermore, many patients prefer not to be entirely surrounded by the CT instrument. C-arm gantries are also capable of imaging a portion of a large object that otherwise would not fit within a traditional CT instrument, The use of C-arm gantries for CT has, however, been limited. Most C-arm gantries "wobble" as they rotate, thus violating the underlying assumptions of the Feldkamp, Kress, and Davis algorithm. The term wobble is used to denote any of a wide range of non-idealities resulting in a non-circular or irregular orbit or orbit portion; including but not limited to: vibration, gravitational sag, mechanical backlash, and other irregularities. The resulting non-circular orbit or orbit portion thus introduces errors into the reconstruction that limit resolution of features inside the object or patient. Nevertheless, Feldkamp backprojection is commonly used to reconstruct images in C-arm gantry systems.

Traditional calibration methods developed with the underlying assumptions of a fixed rotational axis and mid-plane of the x-rays have not begun to address the difficulties of non-circular orbits or orbit portions. For example, Picard et al. (U.S. Pat. No. 5,442,674) teaches the use of a 3D calibration phantom, preferably consisting of a plethora of cellular structures that minimally attenuate X-rays arranged in helix, to calibrate an X-ray system. Rather than addressing non-circular orbits or orbit portions around a patient or object, their method seeks "the intrinsic parameters of the system" when it is "assumed that the imaging system undergoes perfect circular rotation or almost perfect circular rotation."

Others have tried to construct methods which account for non-circular orbits or orbit portions. Fahrig et al. (Med. Phys. 27(1) 30–38) briefly discuss several possible solutions, including reinforcement of the mechanical system to reduce or remove wobble and monitoring the position of the mechanical system during motion through an external system to correct for wobble post-acquisition. Their own approach is discussed in detail and includes the generation of a trigonometric expression describing the position of the gantry. This approach assumes that 1) the motion of the gantry exhibits long term reproducibility, 2) the deviations from a perfect trajectory are small, and 3) the non-idealities due to wobble are either parallel to the axis of rotation or tangential to the circle of rotation and perpendicular to the line joining the x-ray source and the detector plane.

As another example of attempts to correct for wobble in non-circular orbits or orbit portions, Wiesent et al. (U.S. Pat. No. 5,706,324) teach the simultaneous imaging of a patient and a calibration phantom with X-ray computed tomography. While it is stated the annular calibration phantom "permits a precise determination of the photographic geometry," there is no discussion about how this is accomplished.

SUMMARY OF THE INVENTION

Accordingly, one object of this invention is to provide a method and system for the reconstruction of an image through mapping.

Another object is to provide a method and system that allow for the reconstruction of an image formed by an X-ray source and detector that have a non-circular orbit or orbit portions about the patient or object.

A further object of this invention is to provide a method and a device that allow for the reconstruction from projections from any non-circular orbit or orbit portion.

These and other objects are achieved by a method for reconstructing an image of a subject including steps of exposing said subject to x-rays from a source rotated about the subject in an irregular path, obtaining exposure data, and reconstructing the image from the exposure data by mapping a reconstructed image point from a known coordinate. The method may also include a step of exposing the subject using a source mounted on an open C-arm gantry circularly rotated about the subject an irregular path containing non-idealities comprising at least one of wobble of the C-arm, gravitational sag, and vibration, or include steps of generating calibration factors from known coordinates and using the calibration factors in the reconstructing step.

The objects of the invention may also be obtained by an image reconstruction system, having an x-ray source, an x-ray detector disposed to face said source, and means for reconstructing the image from exposure data obtained from the detector by mapping a reconstructed image point from a known coordinate connected to the detector. The source and detector may be mounted on an open C-arm gantry circularly rotated about the subject an irregular path containing non-idealities comprising at least one of wobble of said C-arm, gravitational sag, and vibration.

BRIEF DESCRIPTION OF THE DRAWINGS

A more complete appreciation of the invention and many of the attendant advantages thereof will be readily obtained as the same become better understood by reference to the following detailed description when considered in connection with the accompanying drawings, wherein.

DETAILED DESCRIPTION OF THE PREFERRED EMBODIMENTS

Figure 1A:
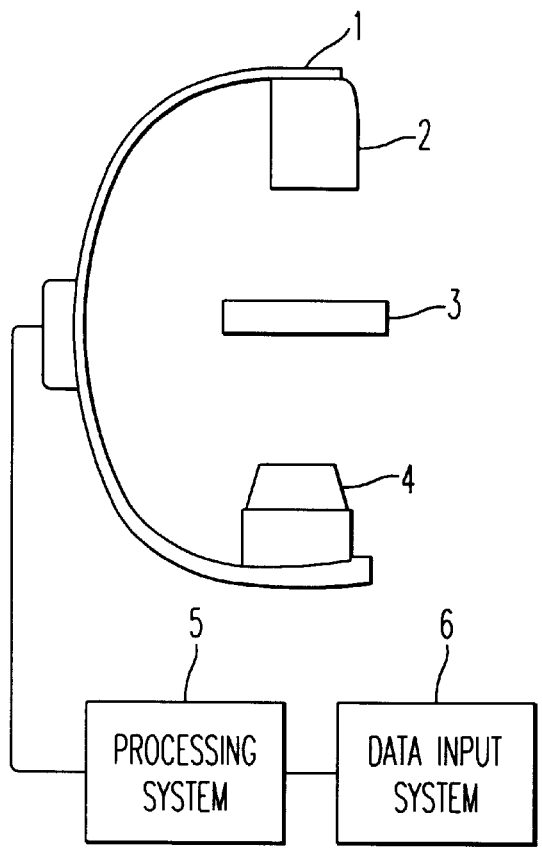
FIG. 1A is a diagram of a C-arm gantry device according to the invention.

FIG. 1A is a diagram of the system according to the invention. The system according to the invention is preferably applied to a C-arm gantry type cone-beam CT system. On a C-shaped gantry 1 an x-ray source device 2 and an x-ray detection device 4 are mounted. X-rays emitted from source 2 are transmitted through a subject (not shown) on bed 3 and are detected by detection device 4, typically a matrix of x-ray sensitive elements of a size such as 512×512 pixels, and can be an image intensifier. Device 4 generates exposure data. The gantry 1 may be suspended on a ceiling support and may be moved along three axes by combining C-arm rotation, C-arm sliding and support column rotation. The support may be moved laterally and longitudinally on the ceiling.

The operation of the system is controlled by a control and processing device 5 and data entry device 6. Device 5 typically includes a computer and handles storing and processing of the exposure data from device 4, and controls and monitors the operation of the system, including the movement of the C-arm and image acquisition and data storage. In particular, device 5 performs reconstruction processing to reconstruct images from the exposure data.

Data entry device 6 allows an operator to input data or commands to operate or monitor the system. Device 6 may typically be a graphical interface having a monitor, keyboard and pointing device. A reconstructed image may also be displayed on the monitor.

The system operates by emitting x-rays that then pass through a subject. The x-rays are detected and exposure data is collected by the processing system. An image is reconstructed using a mapping technique with calibration factors that compensate for non-idealities in the C-arm gantry motion. The calibration factors are preferably obtained with a calibration phantom initially, and then are applied to subsequent image acquisition. The calibration factors are determined as follows.

Figure 1B:
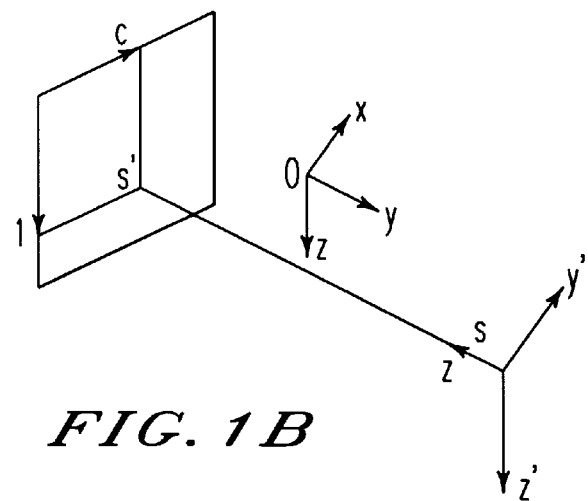
FIG. 1B is a schematic diagram of a CT system geometry.

FIG. 1B shows is a simplified diagram of CT instrument geometry. Point source S emits X-rays that are incident upon three-dimensional object O which can represent a calibration phantom, a patient, a test object, or other article of interest. Possible X-ray sources that can be used to approximate point source S include an x-ray tube. At least a portion of the X-rays generated at point source S pass through or around object O and are received at the detector. The detector can be a planar array of x-ray sensitive elements, such as 512×512 or other X-ray detecting means.

A subject referential R=(O, x, y, z) and a referential R'=(S,x',y',z') associated with the conic projections are defined. FIG. 1B shows source position S and projection S' on the image plane. The column and row position are denoted by c and l on the detector. The center of gravity of the beads, detected in a calibration image corrected for pin cushion distortion, provide the 2D projected positions ($c_i$, $l_i$) of N reference points of the calibration object with known 3D coordinates ($x_i$, $y_i$, $z_i$) in referential R.

By definition, there is a line called the optical axis (or the principal axis) that passes through a point source S that is normal to the detector plane. This optical axis can serve as a basis for the establishment of a coordinate system describing the location of object O and its projections upon detector plane P. All points on the detector plane can be described relative to the point of incidence of the optical axis with the detector plane (also known as the principal point), and points intermediate can be further described by their position along the axis. The particular notation that will be used throughout the remainder of this description will include:

referring to points on the detector plane as substantially two-dimensional area elements called pixels, each pixel having a column location c and a row location l;

referring to points intermediate to the source S and the detector plane as three-dimensional volume elements called voxels, each voxel having an x-coordinate x, a y-coordinate y, and a z-coordinate z.

Figure 2:
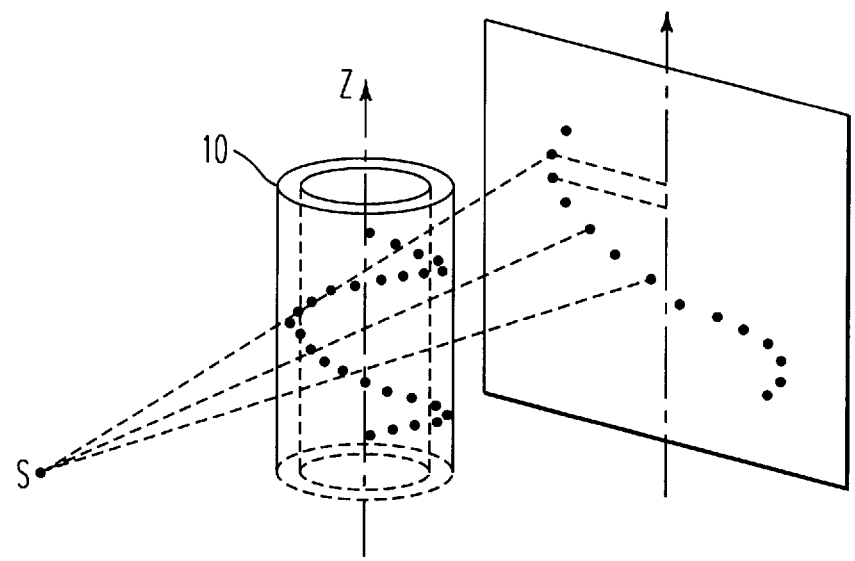
FIG. 2 is a diagram of a calibration phantom that can be used in conjunction with the method according to the invention.

FIG. 2 illustrates an example calibration phantom 10 that can be used as object O to generate the calibration factors according to the present invention. An example is taught by U.S. Pat. No. 5,442,674 to Picard et al. A series of nearly spherical beads is arranged in a supporting matrix such that the location of the beads within the matrix is known and the radiographic contrast between the beads and the supporting matrix is large enough to allow the beads to be resolved in an X-ray projection. The beads are also provided with one or more distinguishing characteristics so that they can be identified on an X-ray projection.

The calibration phantom used in this embodiment is a tungsten carbide bead phantom, with the beads arranged in helical trajectory. The center of each bead is determined to a sub-pixel accuracy. The largest pellet is identified on the projections and is used to order the remaining pellets. The ordered set of pellets in the projections are then matched with the known 3D pellet positions.

Thus, when such a calibration phantom is projected upon detector plane P, the x-coordinate x, the y-coordinate y, and the z-coordinate z of a voxel located substantially at the center of each spherical bead is known, as is the column location c and a row location l of an associated pixel located substantially at the center of each bead projection.

A relationship between factors x, y, z, c, and l is given by:

$$\lambda[cl1]^T = M[xyz1]^T \quad (1)$$

where the superscript T denotes the transpose of the position vectors [cl1] and [xyz1], and M denotes a calibration matrix having matrix elements m11, m12, m13, m14, m21, m22, m23, m24, m31, m32, m33, and m34, also known as calibration factors, and λ represents a scaling factor in the homogeneous coordinate system.

The calibration matrix (and hence the calibration factors) remain constant for every bead in the calibration matrix for a single position of the source, detector, and calibration phantom system. Thus, by using a phantom with a number of beads where the position of the beads is known beforehand and the position of the projection from each bead onto the detector plane can be determined, a series simultaneous equation can be written. If a sufficient number of such simultaneous equations is available, the calibration matrix and its calibration factors can be determined.

The current invention relates to determining and storing a calibration matrix and calibration factors for various positions of the source, detector, and calibration phantom system. With this approach, there is no constraint upon the nature of the system, i.e., the source and detector are not constrained to revolve around the phantom in a circular or substantially circular geometry. Furthermore, there is no requirement that the source and detector complete an orbit about the phantom. This approach is especially useful in applications such as CT-imaging with a C-arm gantry, where access to a patient is desired and exact circular orbits difficult to achieve.

Solving for the calibration factors that constitute the calibration matrix can be done as follows. Equation (1) may be rewritten as a series of simultaneous equations for a number N of volume elements i of the calibration phantom, given as (2)

$$0 = (m_{11} - m_{31}c_i)x_i + (m_{12} - m_{32}c_i)y_i + (m_{13} - m_{33}c_i)z_i + (m_{14} - m_{34}c_i)$$

$$0 = (m_{21} - m_{31}l_i)x_i + (m_{22} - m_{32}l_i)y_i + (m_{23} - m_{33}l_i)z_i + (m_{24} - m_{34}l_i) \quad (2)$$

The simultaneous equations in (2) are used to estimate the elements of matrix M using the classical unconstrained method. The method estimates the elements of matrix M which represents the linear transformation in homogeneous coordinates associated to the conic projection. Then equations (2) can be rewritten as (3).

$$0 = m_{11}x_i + m_{12}y_i + m_{13}z_i + m_{14} - m_{31}(c_ix_i) - m_{32}(c_iy_i) - m_{33}(c_iz_i) - (m_{34}c_i)$$

$$0 = m_{21}x_i + m_{22}y_i + m_{23}z_i + m_{24} - m_{31}(l_ix_i) - m_{32}(l_iy_i) - m_{33}(l_iz_i) - (m_{34}l_i) \quad (3)$$

The term m34 can be taken as unity due to the homogeneous coordinates and equations (3) can be expressed as equations (4)

$$c_i = m_{11}x_i + m_{12}y_i + m_{13}z_i + m_{14} - m_{31}(c_ix_i) - m_{32}(c_iy_i) - m_{33}(c_iz_i)$$

$$l_i = m_{21}x_i + m_{22}y_i + m_{23}z_i + m_{24} - m_{31}(l_ix_i) - m_{32}(l_iy_i) - m_{33}(l_iz_i)) \quad (4)$$

In equation (4), the $(c_i, l_i)$ are the centers of the beads obtained from the projection images. These equations can be placed in matrix form as equations (5) and (6).

$$\begin{bmatrix} x_1 & y_1 & z_1 & 1 & -c_1x_1 & -c_1y_1 & -c_1z_1 \\ x_2 & y_2 & z_2 & 1 & -c_2x_2 & -c_2y_2 & -c_2z_2 \\ \vdots & \vdots & \vdots & \vdots & & & \\ \vdots & \vdots & \vdots & \vdots & & & \\ x_N & y_N & z_N & 1 & -c_Nx_N & -c_Ny_N & -c_Nz_N \end{bmatrix}_{Nx7} \begin{bmatrix} m_{11} \\ m_{12} \\ m_{13} \\ m_{14} \\ m_{31} \\ m_{32} \\ m_{33} \end{bmatrix}_{7x1} = \begin{bmatrix} c_1 \\ c_2 \\ c_3 \\ \vdots \\ \vdots \\ \vdots \\ c_1 \end{bmatrix}_{Nx1} \quad (5)$$

$$\begin{bmatrix} x_1 & y_1 & z_1 & 1 & -l_1x_1 & -l_1y_1 & -l_1z_1 \\ x_2 & y_2 & z_2 & 1 & -l_2x_2 & -l_2y_2 & -l_2z_2 \\ \vdots & \vdots & \vdots & \vdots & & & \\ \vdots & \vdots & \vdots & \vdots & & & \\ x_N & y_N & z_N & 1 & -l_Nx_N & -l_Ny_N & -l_Nz_N \end{bmatrix}_{Nx7} \begin{bmatrix} m_{21} \\ m_{22} \\ m_{23} \\ m_{24} \\ m_{31} \\ m_{32} \\ m_{33} \end{bmatrix}_{7x1} = \begin{bmatrix} l_1 \\ l_2 \\ l_3 \\ \vdots \\ \vdots \\ \vdots \\ l_N \end{bmatrix}_{Nx1} \quad (6)$$

Equations (5) and (6) are represented in a general form by $$AC = B \quad (7)$$

where A is not a square matrix but of dimension (N×7) where N is the number of equations and the number of beads used from the calibration phantom, and where C is now a vector containing seven elements (calibration factors) of the original calibration matrix M. Since there are only seven factors present in each of equations (5) and (6), only two sets of seven simultaneous equations need to be solved to determined the calibration matrix M. Solving for the vector C using the two sets of simultaneous equations given in equations (5) and (6) can be done as in equation (8), where $$C = (A^T A)^{-1} A^T B \quad (8)$$

Since the calibration factors m31, m32, and m33 are present in both sets of simultaneous equations (5) and (6), several options are available at this point. Among these, one option is to eliminate the distinctions between equations (5) and (6) and solve the combined 2N equations simultaneously. This will generate the calibration matrix M that can be used as in equation (1) to describe the relationship between a projection and an object.

Alternatively, m31, m32, m33, and m34 in equations (6) can be replaced by calibration factors m41, m42, m43, and m44 as shown in (9), and sets of equations (5) and (6) can be solved independently. This will significantly reduce computational difficulty, including round-off error arising from inverting large matrices. Keeping equations (5) and (6) separated yields two calibration vectors. The first calibration vector is specifically directed toward the relationship between the column location of a pixel and the x-coordinate, y-coordinate, and z-coordinate of a voxel, and is given in equation (5) above, although m31, m32, m33, and m34 no longer correspond strictly to the matrix elements of calibration matrix M in the prior art. The second calibration vector is specifically directed toward the relationship between the row location of a pixel and the x-coordinate, y-coordinate, and z-coordinate of a voxel, and is given in equation (9) below.

$$\begin{bmatrix} x_1 & y_1 & z_1 & 1 & -l_1x_1 & -l_1y_1 & -l_1z_1 \\ x_2 & y_2 & z_2 & 1 & -l_2x_2 & -l_2y_2 & -l_2z_2 \\ \vdots & \vdots & \vdots & \vdots & & & \\ \vdots & \vdots & \vdots & \vdots & & & \\ x_N & y_N & z_N & 1 & -l_Nx_N & -l_Ny_N & -l_Nz_N \end{bmatrix}_{Nx7} \begin{bmatrix} m_{21} \\ m_{22} \\ m_{23} \\ m_{24} \\ m_{41} \\ m_{42} \\ m_{43} \end{bmatrix}_{7x1} = \begin{bmatrix} l_1 \\ l_2 \\ l_3 \\ \vdots \\ \vdots \\ \vdots \\ l_N \end{bmatrix}_{Nx1} \quad (9)$$

Once the values of the calibration matrix C are obtained, then $(c_i, l_i)$, the image coordinate of a reprojected point can be calculated from the known position $(x_i, y_i, z_i)$ using equations (10) and (11) as follows:

$$c_i = \frac{m_{11}x_i + m_{12}y_i + m_{13}z_i + m_{14}}{m_{31}x_i + m_{32}y_i + m_{33}z_i + m_{34}} \quad (10)$$

$$l_i = \frac{m_{21}x_i + m_{22}y_i + m_{23}z_i + m_{24}}{m_{41}x_i + m_{42}y_i + m_{43}z_i + m_{44}} \quad (11)$$

Equation (4) may be solved after splitting into equations (5) and (6) for two purposes. First, the values generated by m31, m32 and m33 by equations (5) and (6) were expected to be equal and, second, instead of inverting a larger matrix less round-off error may be expected by inverting smaller matrices. However, the values of m31, m32 and m33 obtained from equations (3) and (4) differed, which may be resolved by replacing the m3's by the m4's of equation (4) in equation (7). Another alternative is to solve the elements of the matrix from one set of equations which allows better interaction between the variables.

$$\begin{bmatrix} x_1 & y_1 & z_1 & 1 & 0 & 0 & 0 & 0 & -c_1x_1 & -c_1y_1 & -c_1z_1 \\ & \vdots & & & & \vdots & & & & \vdots & \\ 0 & 0 & 0 & 0 & x_1 & y_1 & z_1 & 1 & -l_1x_1 & -l_1y_1 & -l_1z_1 \\ & \vdots & & & & \vdots & & & & \vdots & \end{bmatrix}_{2N \times 11} \quad (12)$$

$$\begin{bmatrix} m_{11} \\ m_{12} \\ m_{13} \\ m_{14} \\ m_{21} \\ m_{22} \\ m_{23} \\ m_{24} \\ m_{31} \\ m_{32} \\ m_{33} \end{bmatrix} = \begin{bmatrix} c_1 \\ c_2 \\ \vdots \\ \vdots \\ \vdots \\ c_N \\ l_1 \\ \vdots \\ \vdots \\ \vdots \\ l_N \end{bmatrix}_{2N \times 1}$$

Equations (10) and (11) are rewritten as equations (13) and (14) as follows, using only 11 parameters:

$$c_i = \frac{m_{11}x_i + m_{12}y_i + m_{13}z_i + m_{14}}{m_{31}x_i + m_{32}y_i + m_{33}z_i + m_{34}} \quad (13)$$

$$l_i = \frac{m_{21}x_i + m_{22}y_i + m_{23}z_i + m_{24}}{m_{31}x_i + m_{32}y_i + m_{33}z_i + m_{34}} \quad (14)$$

Examples of calibration factors obtained by the above procedure are given in FIGS. 3–12. These calibration factors were obtained on a C-arm gantry system at various gantry positions, indicated as frame number.

In the method according to the invention, the calibration factors are determined for all possible gantry x, y and z coordinates of the subject. The mapping allows one to determine where is the appropriate data for every voxel of the subject. The image may be reconstructed accurately without the distortions of the c-arm gantry.

Figure 14:
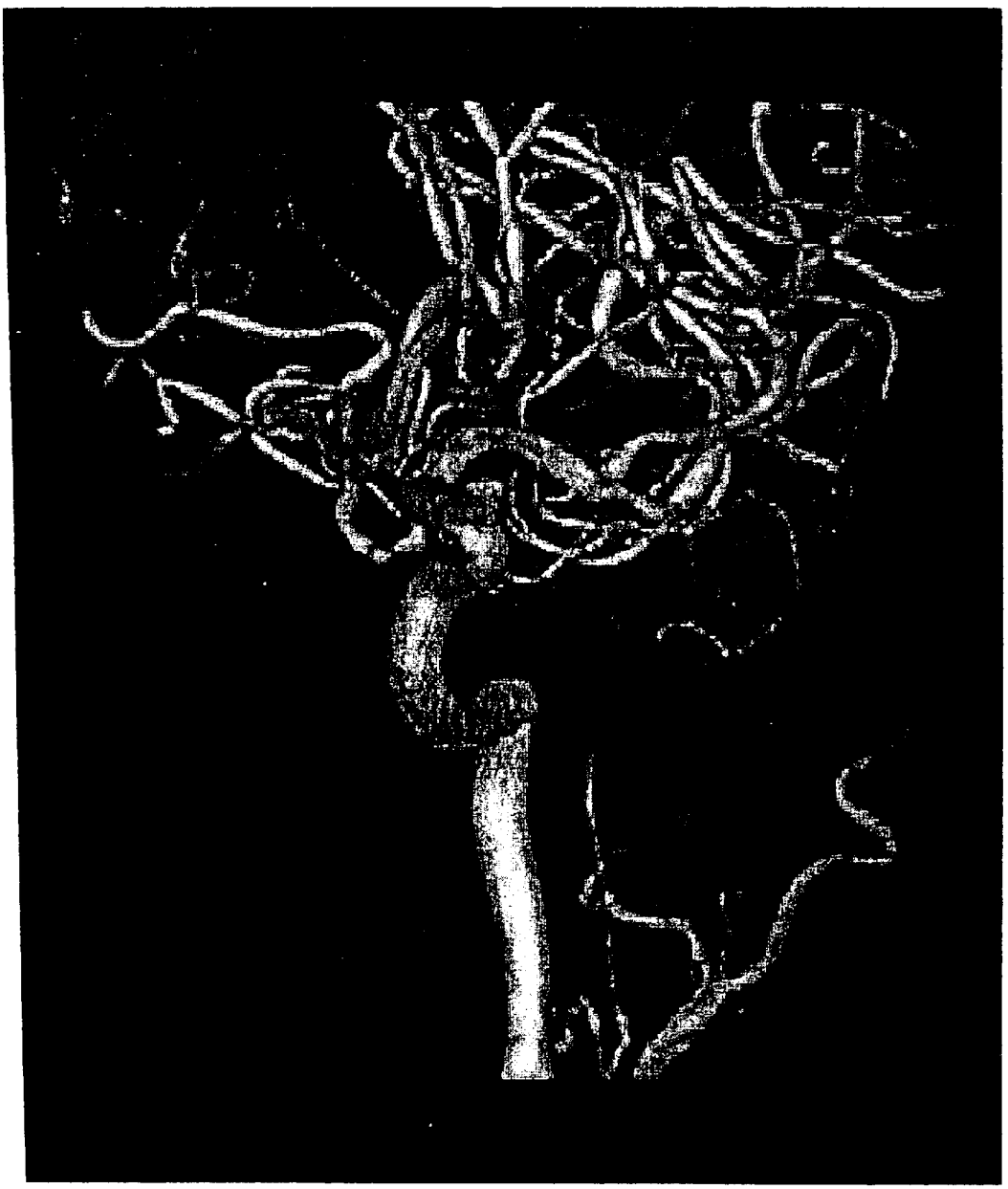
FIG. 14 is an image reconstructed according to the invention.

FIG. 14 shows a image of a carotid artery reconstructed using the method and system according to the invention. The image was obtained using contrast media injected into the blood stream. The image is free from the distortions and artifacts that arise when reconstructing the image using the conventional approach, such as Feldkamp reconstruction on a c-arm gantry.

Figure 13:
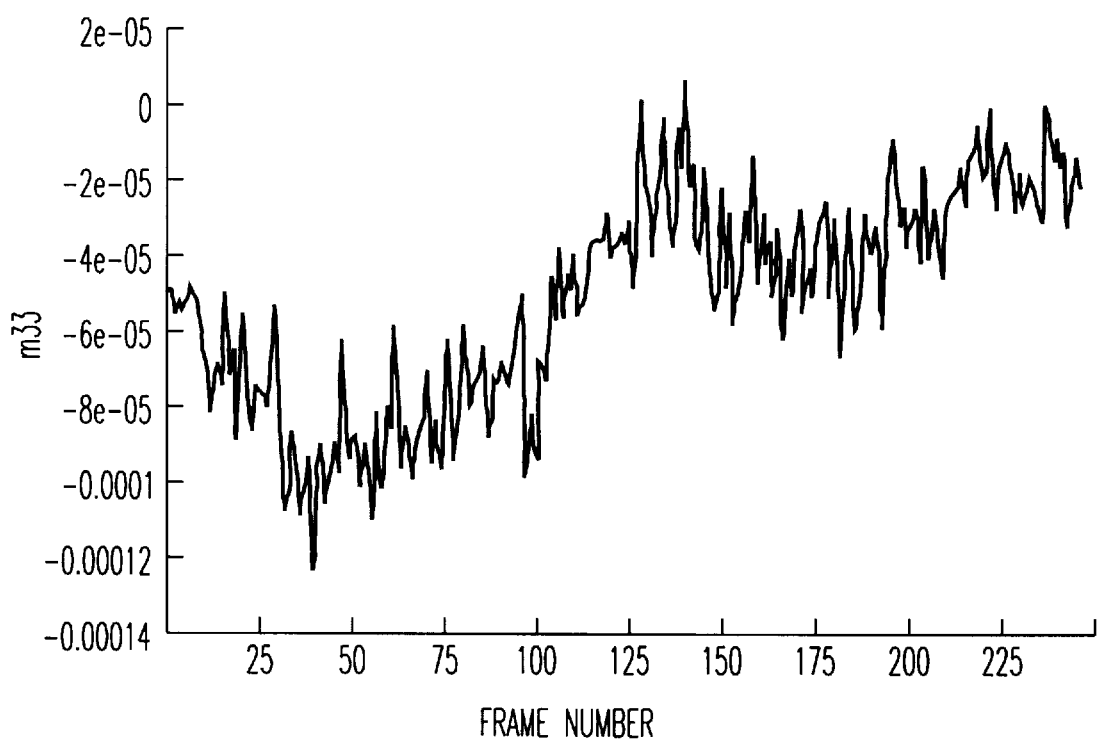
FIG. 13 is a graph of the value of calibration factor m33 at different gantry positions.
Figure 3:
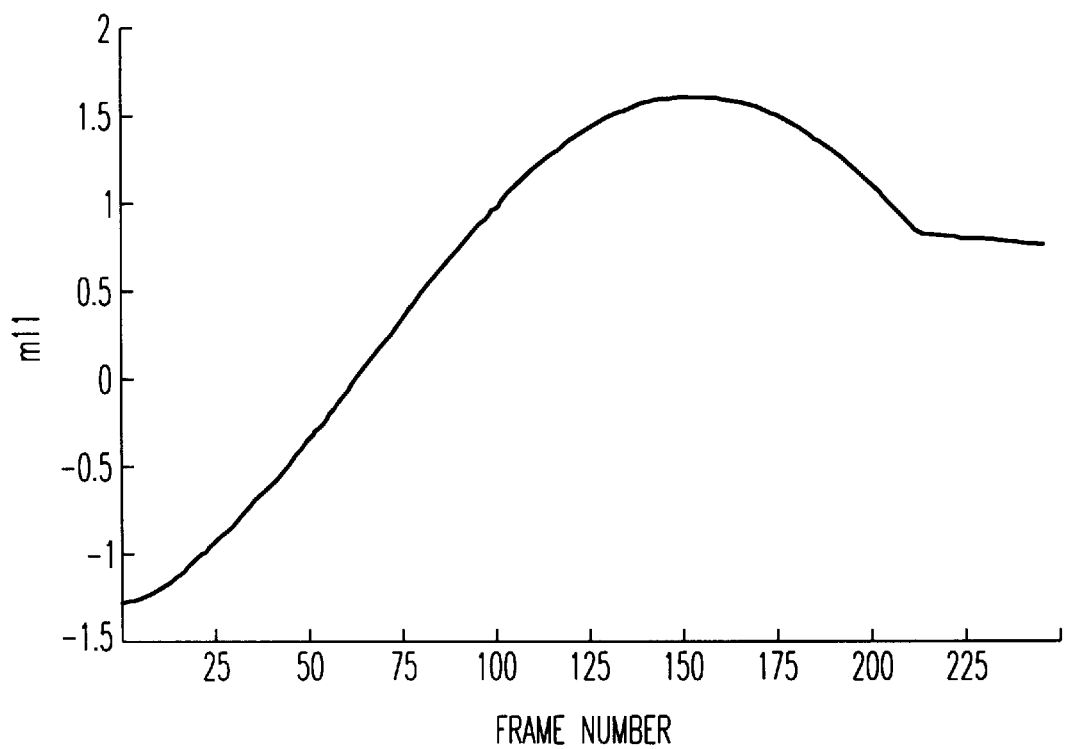
FIG. 3 is a graph of the value of calibration factor m11 at different gantry positions.
Figure 4:
FIG. 4 is a graph of the value of calibration factor m12 at different gantry positions.
Figure 5:
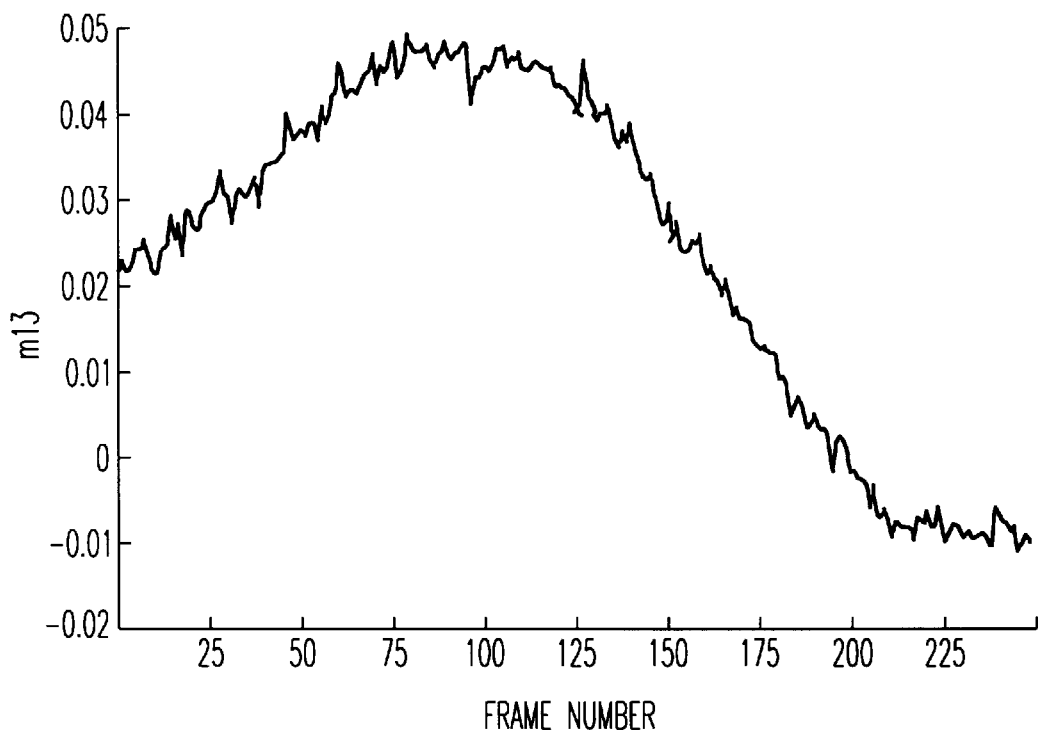
FIG. 5 is a graph of the value of calibration factor m13 at different gantry positions.
Figure 6:
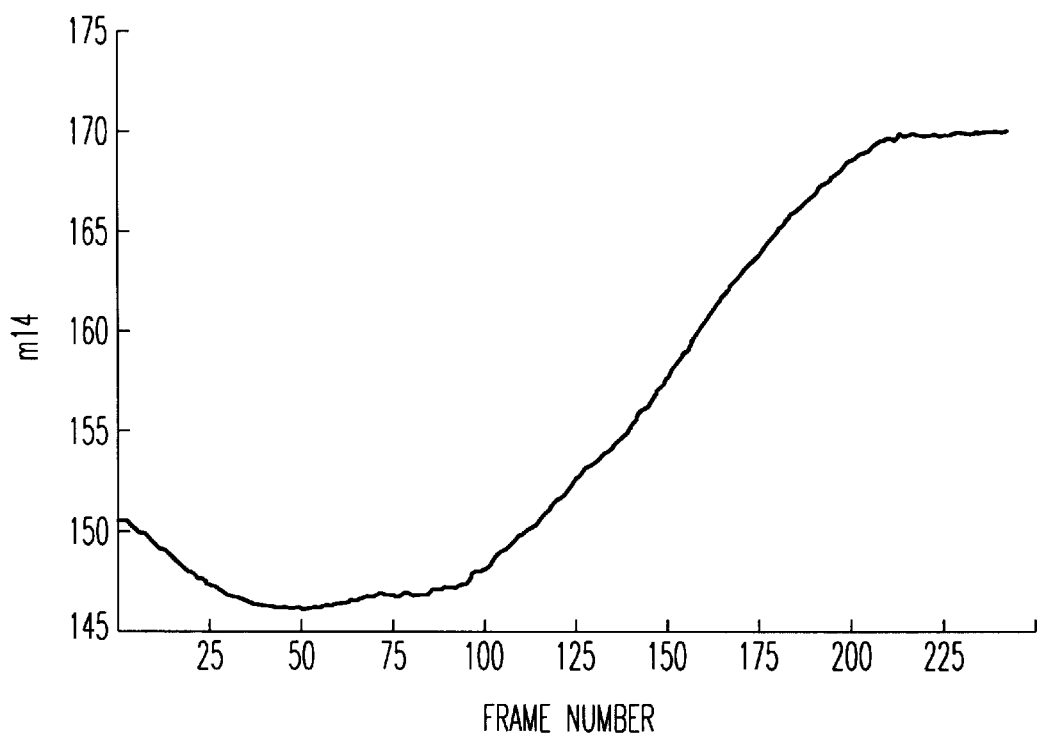
FIG. 6 is a graph of the value of calibration factor m14 at different gantry positions.
Figure 7:
FIG. 7 is a graph of the value of calibration factor m21 at different gantry positions.
Figure 8:
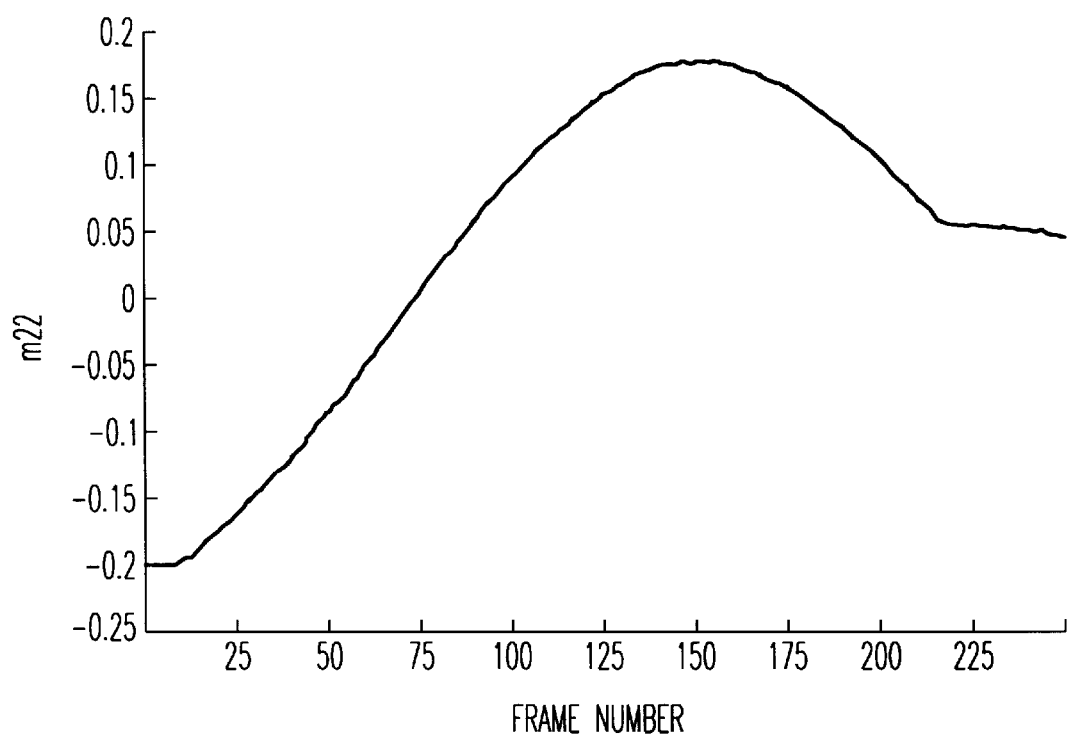
FIG. 8 is a graph of the value of calibration factor m22 at different gantry positions.
Figure 9:
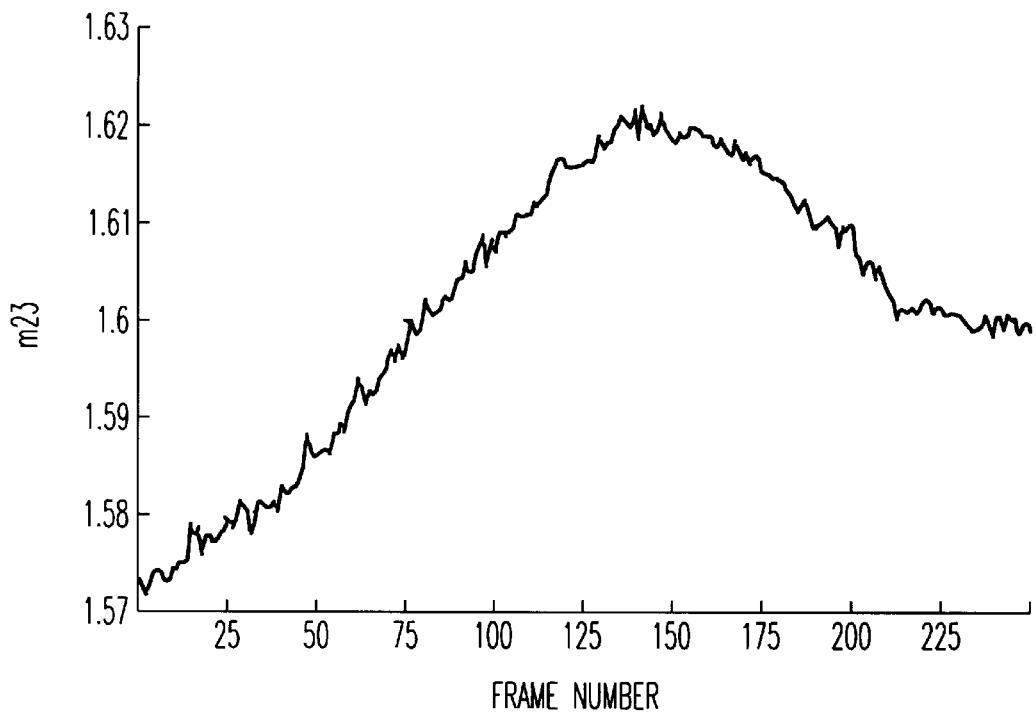
FIG. 9 is a graph of the value of calibration factor m23 at different gantry positions.
Figure 10:
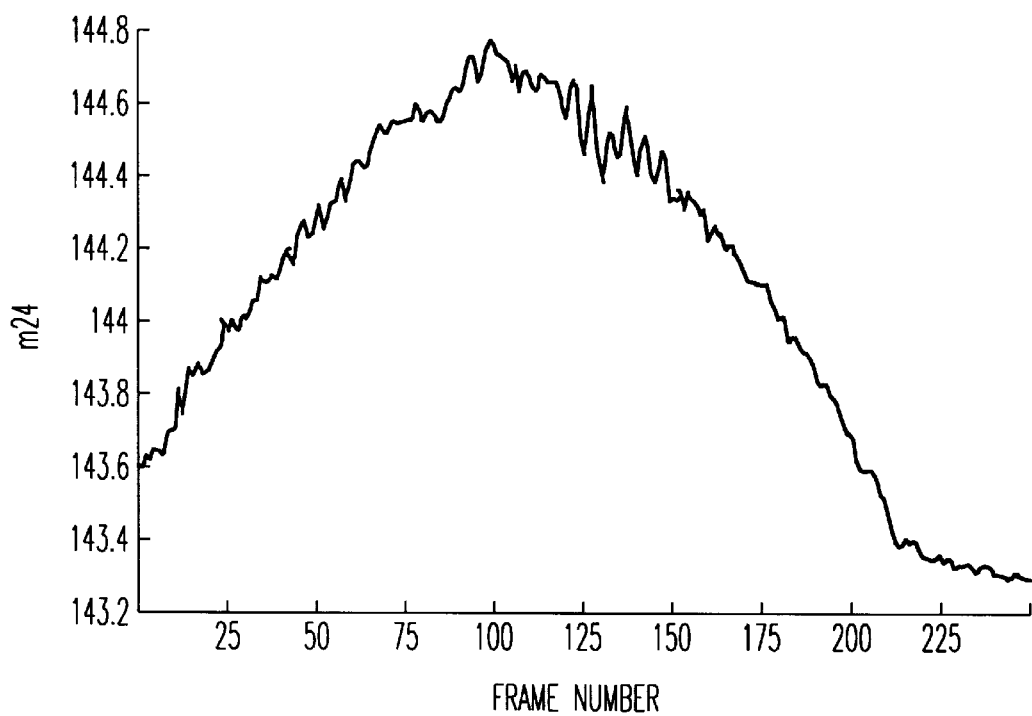
FIG. 10 is a graph of the value of calibration factor m24 at different gantry positions.
Figure 11:
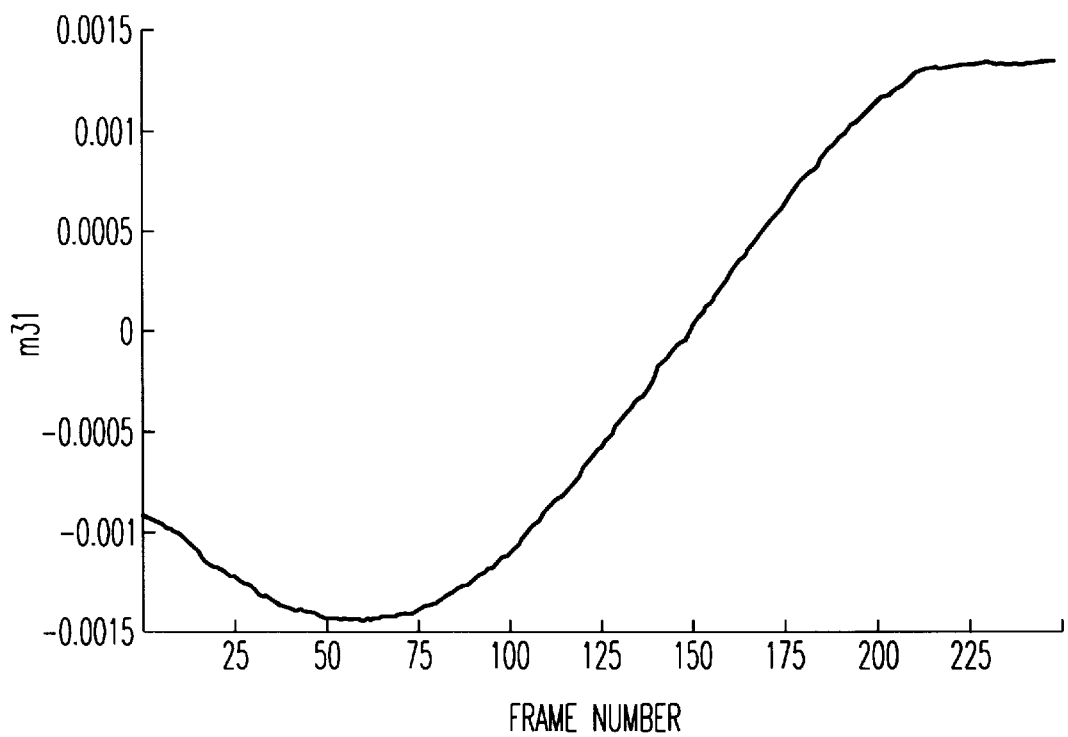
FIG. 11 is a graph of the value of calibration factor m31 at different gantry positions.
Figure 12:
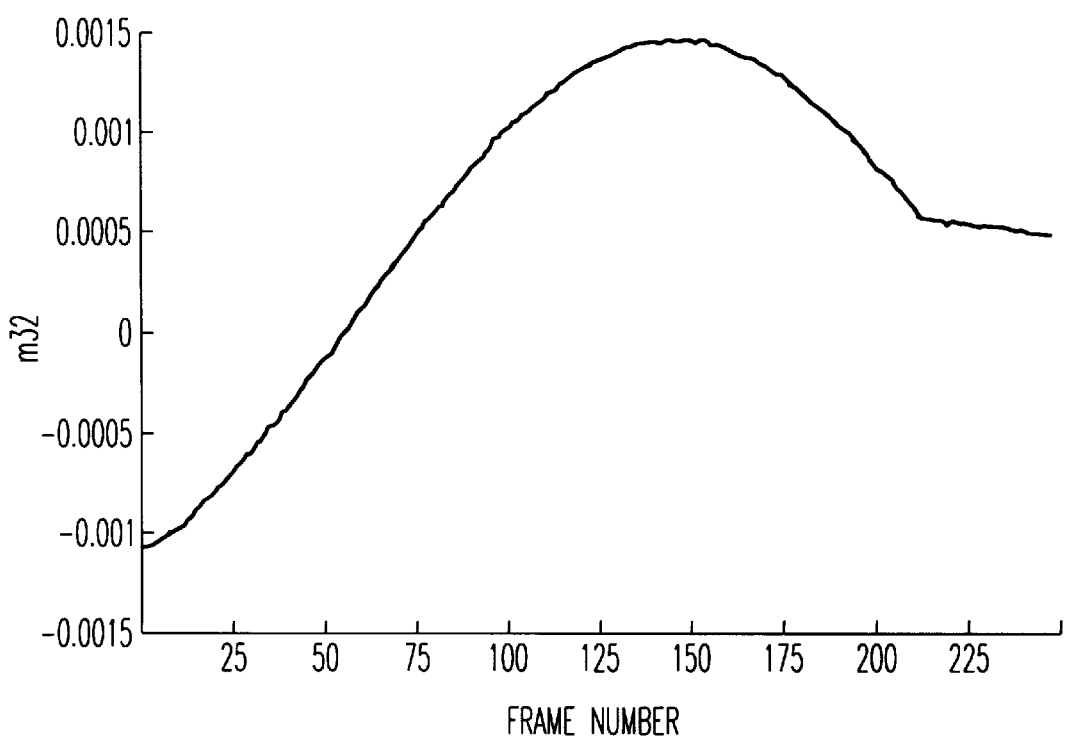
FIG. 12 is a graph of the value of calibration factor m32 at different gantry positions.

In a second embodiment, the mapping uses a Taylor expansion and approximations for the column and row indices on a data frame corresponding to the image voxel are determined. Starting with equations (13) and (14) the following approximations simplify the reconstruction computation. The approximations use the assumption that m33 is very small. A graph of m33 is shown in FIG. 13, demonstrating the assumption to be correct.

$$c \approx a_0(\beta, x, y) + a_1(\beta, x, y)z \quad (15)$$

and $$l \approx b_0(\beta, x, y) + b_1(\beta, x, y)z + b_2(\beta, x, y)z^2 \quad (16)$$

where $$U(\beta, x, y) = m_{31}x + m_{32}y + m_{34} \quad (17)$$

$$a_0(\beta, x, y) = \frac{m_{11}x + m_{12}y + m_{14}}{U} \quad (18)$$

-continued $$a_1(\beta, x, y) + \frac{1}{U}(m_{13} - m_{33}a_0) = \frac{m_{13}}{U} - \frac{m_{33}(m_{11}x + m_{12}y + m_{14})}{U^2} \quad (19)$$

$$b_o(\beta, x, y) = \frac{m_{21}x + m_{22}y + m_{24}}{U} \quad (20)$$

$$b_1(\beta, x, y) = \frac{1}{U}(m_{32} - m_{33}b_0) = \frac{m_{23}}{U} - \frac{m_{33}(m_{21}x + m_{22}y + m_{24})}{U^2} \quad (21)$$

$$b_2(\beta, x, y) = \frac{-m_{33}}{U}b_1 = \frac{(m_{21}x + m_{22}y + m_{24})m_{33}^2}{U^3} - \frac{m_{23}m_{33}}{U^2} \quad (22)$$

Equations (15) and (16) may be implemented in software by additions, without multiplications. The computational time for reconstructing the image is thus made much more efficient. Assuming that the z-calculation is in the innermost loop, and a uniform increment in z, $\Delta z$, equations (15) and (16) may be rewritten as:

$$c_n = a_0 + a_1 z_n \quad (23)$$

or iteratively, as $$c_n = c_{n-1} + a_1 \Delta z \quad (25)$$

$$\begin{aligned} l_n - l_{n-1} &= b_1 \Delta z + b_2(z_n^2 - z_{n-1}^2) \\ &= b_1 \Delta z + b_2(z_n - z_{n-1})(z_n + z_{n-1}) \\ &= b_1 \Delta z + b_2 \Delta z (z_n + z_n - \Delta z) \\ &= b_1 \Delta z + 2 b_2 z_n \Delta z - b_2 \Delta z^2 \end{aligned} \quad (26)$$

Equation (26) may be rewritten as:

$$l_n = l_{n-1} + \Delta l_n \quad (27)$$

where $$\Delta l_n = \Delta l_{n-1} + 2b_2 \Delta z^2 \quad (28)$$

with initial conditions $$l_0 = b_0 + b_1 z_0 + b_2 \quad (29)$$

and $$\Delta l_0 = b_1 \Delta z + 2 b_2 z_0 \quad (30)$$

Obviously, numerous modifications and variations of the present invention are possible in light of the above teachings. For example, the present invention may be implemented in the form of software stored on a recording medium, i.e., a computer program product. It is therefore to be understood that within the scope of the appended claims, the invention may be practiced otherwise than as specifically described herein.

What is claimed as new and desired to be secured by Letters Patent of the United States is:

1. A method for reconstructing an image of a subject, comprising:

exposing said subject to x-rays from a source rotated about said subject in an irregular path;

obtaining exposure data;

reconstructing said image from said exposure data by mapping a reconstructed image point from a known coordinate; and determining image coordinates $(c_i, l_i)$ of a reprojected point from a known position $(x_i, y_i, z_i)$ using:

$$c_i = \frac{m_{11} x_i + m_{12} y_i + m_{13} z_i + m_{14}}{m_{31} x_i + m_{32} y_i + m_{33} z_i + m_{34}}$$

$$l_i = \frac{m_{21} x_i + m_{22} y_i + m_{23} z_i + m_{24}}{m_{41} x_i + m_{42} y_i + m_{43} z_i + m_{44}}$$

where: m11, m12 . . . m44 are calibration factors.

2. A method as recited in claim 1, comprising:
exposing said subject using a source mounted on an open C-arm gantry circularly rotated about said subject an irregular path containing non-idealities comprising at least one of wobble of said C-arm, gravitational sag, and vibration.

3. A method as recited in claim 1, comprising:
generating calibration factors from known coordinates; and
using said calibration factors in said reconstructing step.

4. A device as recited in claim 1, comprising:
determining said calibration factors using:

$$\begin{bmatrix} x_1 & y_1 & z_1 & l & -c_1 x_1 & -c_1 y_1 & -c_1 z_1 \\ x_2 & y_2 & z_2 & l & -c_2 x_2 & -c_2 y_2 & -c_2 z_2 \\ \vdots & \vdots & & \vdots & & & \vdots \\ \vdots & \vdots & & \vdots & & & \vdots \\ x_i & y_i & z_i & l & -c_i x_i & -c_i y_i & -c_i z_i \end{bmatrix}_{ix7} \begin{bmatrix} m_{11} \\ m_{12} \\ m_{13} \\ m_{14} \\ m_{31} \\ m_{32} \\ m_{33} \end{bmatrix}_{7x1} = \begin{bmatrix} c_1 \\ c_2 \\ c_3 \\ \vdots \\ \vdots \\ \vdots \\ c_i \end{bmatrix}_{ix1} \text{ and}$$

$$\begin{bmatrix} x_1 & y_1 & z_1 & l & -l_1 x_1 & -l_1 y_1 & -l_1 z_1 \\ x_2 & y_2 & z_2 & l & -l_2 x_2 & -l_2 y_2 & -l_2 z_2 \\ \vdots & \vdots & & \vdots & & & \vdots \\ \vdots & \vdots & & \vdots & & & \vdots \\ x_i & y_i & z_i & l & -l_i x_i & -l_i y_i & -l_i z_i \end{bmatrix}_{ix7} \begin{bmatrix} m_{21} \\ m_{22} \\ m_{23} \\ m_{24} \\ m_{31} \\ m_{32} \\ m_{33} \end{bmatrix}_{7x1} = \begin{bmatrix} l_1 \\ l_2 \\ l_3 \\ \vdots \\ \vdots \\ \vdots \\ l_i \end{bmatrix}_{ix1}$$

where $c_i$ is the column position and $l_i$ is the row position of an area element i, and $x_i$, $y_i$, and $z_i$ are respectively an x-coordinate, a y-coordinate, and a z-coordinate for an associated volume element i.

5. A method as recited in claim 1, comprising:
imaging a calibration phantom having a plurality of calibration volume elements;
identifying a plurality of calibration area elements in a calibration phantom image;
matching said calibration area elements with said calibration volume elements of said calibration phantom; and
calculating a plurality of mapping coefficients based upon the spatial relationship between said area elements and said calibration volume elements.

6. A method as recited in claim 5, comprising:
calculating said plurality of mapping coefficients at a plurality of locations along said irregular path associated with each plurality of calibration factors.

7. A method as recited in claim 1, wherein said reconstructing step comprises:
selecting an active area element from said plurality of calibration area elements along with a matched volume element from said plurality of calibration volume elements; and
describing a mathematical relationship between said active area element and said matched volume element.

8. A method as recited in claim 7, comprising:
identifying a column location and a row location for said active area element;
identifying an x-coordinate, a y-coordinate, and a z-coordinate for said matched volume element; and
relating said column location, said row location, said x-coordinate, said y-coordinate, and said z-coordinate.

9. A method for reconstructing an image of a subject, comprising:
exposing said subject to x-rays from a source rotated about said subject in an irregular path;
obtaining exposure data;
reconstructing said image from said exposure data by mapping a reconstructed image point from a known coordinate; and
determining image coordinates ($c_i$, $l_i$) of a reprojected point from a known position ($x_i, y_i, z_i$) using:

$$c_i = \frac{m_{11} x_i + m_{12} y_i + m_{13} z_i + m_{14}}{m_{31} x_i + m_{32} y_i + m_{33} z_i + m_{34}}$$

$$l_i = \frac{m_{21} x_i + m_{22} y_i + m_{23} z_i + m_{24}}{m_{31} x_i + m_{32} y_i + m_{33} z_i + m_{34}}$$

where: m11, m12, . . . m34 are calibration factors.

10. A method as recited in claim 9, comprising:
determining said calibration factors using:

$$\begin{bmatrix} x_1 & y_1 & z_1 & 1 & 0 & 0 & 0 & 0 & -c_1 x_1 & -c_1 y_1 & -c_1 z_1 \\ \vdots & & & & \vdots & & & & \vdots & & \vdots \\ 0 & 0 & 0 & 0 & x_1 & y_1 & z_1 & 1 & -l_1 x_1 & -l_1 y_1 & -l_1 z_1 \\ \vdots & & & & \vdots & & & & \vdots & & \vdots \end{bmatrix}_{2Nx11} \begin{bmatrix} m_{11} \\ m_{12} \\ m_{13} \\ m_{14} \\ m_{21} \\ m_{22} \\ m_{23} \\ m_{24} \\ m_{31} \\ m_{32} \\ m_{33} \end{bmatrix} = \begin{bmatrix} c_1 \\ c_2 \\ \vdots \\ \vdots \\ c_N \\ l_1 \\ \vdots \\ l_N \end{bmatrix}_{2Nx1}$$

where $c_i$ is the column position and $l_i$ is the row position of an area element i, and $x_i$, $y_i$, and $z_i$ are respectively an x-coordinate, a y-coordinate, and a z-coordinate for an associated volume element i.

11. A method for reconstructing an image of a subject, comprising:
exposing said subject to x-rays from a source rotated about said subject in an irregular path;
obtaining exposure data;

reconstructing said image from said exposure data by mapping a reconstructed image point from a known coordinate; and determining image coordinates (c, l) of a reprojected point from a known position (x,y,z) at angle $\beta$ using:

$$c \approx a_0(\beta,x,y) + a_1(\beta,x,y)z$$

and $$l \approx b_0(\beta,x,y) + b_1(\beta,x,y)z + b_2(\beta,x,y)z^2$$

where $$U(\beta,x,y) = m_{31}x + m_{32}y + m_{34}$$

$$a_0(\beta, x, y) = \frac{m_{11}x + m_{12}y + m_{14}}{U}$$

$$a_1(\beta, x, y) + \frac{1}{U}(m_{13} - m_{33}a_0) = \frac{m_{13}}{U} - \frac{m_{33}(m_{11}x + m_{12}y + m_{14})}{U^2}$$

$$b_o(\beta, x, y) = \frac{m_{21}x + m_{22}y + m_{24}}{U}$$

$$b_1(\beta, x, y) = \frac{1}{U}(m_{32} - m_{33}b_0) = \frac{m_{23}}{U} - \frac{m_{33}(m_{21}x + m_{22}y + m_{24})}{U^2}$$

and $$b_2(\beta, x, y) = \frac{-m_{33}}{U}b_1 = \frac{(m_{21}x + m_{22}y + m_{24})m_{33}^2}{U^3} - \frac{m_{23}m_{33}}{U^2}.$$

12. An image reconstruction device, comprising:

an x-ray source;

an x-ray detector disposed to face said source;

means for reconstructing said image from exposure data obtained from said detector by mapping a reconstructed image point from a known coordinate connected to said detector; and means for determining image coordinates (c, l) of a reprojected point from a known position (x,y,z) at angle $\beta$ using:

$$c \approx a_0(\beta,x,y) + a_1(\beta,x,y)z$$

and $$l \approx b_0(\beta,x,y) + b_1(\beta,x,y)z + b_2(\beta,x,y)z^2$$

where $$U(\beta,x,y) = m_{31}x + m_{32}y + m_{34}$$

$$a_0(\beta, x, y) = \frac{m_{11}x + m_{12}y + m_{14}}{U}$$

$$a_1(\beta, x, y) + \frac{1}{U}(m_{13} - m_{33}a_0) = \frac{m_{13}}{U} - \frac{m_{33}(m_{11}x + m_{12}y + m_{14})}{U^2}$$

$$b_o(\beta, x, y) = \frac{m_{21}x + m_{22}y + m_{24}}{U}$$

$$b_1(\beta, x, y) = \frac{1}{U}(m_{32} - m_{33}b_0) = \frac{m_{23}}{U} - \frac{m_{33}(m_{21}x + m_{22}y + m_{24})}{U^2}$$

and $$b_2(\beta, x, y) = \frac{-m_{33}}{U}b_1 = \frac{(m_{21}x + m_{22}y + m_{24})m_{33}^2}{U^3} - \frac{m_{23}m_{33}}{U^2}.$$

13. An image reconstruction device, comprising:

an x-ray source;

an x-ray detector disposed to face said source; and means for reconstructing said image from exposure data obtained from said detector by mapping a reconstructed image point from a known coordinate connected to said detector;

wherein said means comprises means for determining image coordinates $(c_i, l_i)$ of a reprojected point from a known position $(x_i, y_i, z_i)$ using:

$$c_i = \frac{m_{11}x_i + m_{12}y_i + m_{13}z_i + m_{14}}{m_{31}x_i + m_{32}y_i + m_{33}z_i + m_{34}}$$

$$l_i = \frac{m_{21}x_i + m_{22}y_i + m_{23}z_i + m_{24}}{m_{41}x_i + m_{42}y_i + m_{43}z_i + m_{44}}$$

where: m11, m12, ... m44 are calibration factors.

14. A device as recited in claim 13, comprising:

said source and detector being mounted on an open C-arm gantry circularly rotated about said subject an irregular path containing non-idealities comprising at least one of wobble of said C-arm, gravitational sag, and vibration.

15. A device as recited in claim 13, wherein said means comprises a computer connected to said detector configured to reconstruct said image from exposure data obtained from said detector by mapping said reconstructed image point from said known coordinate.

16. A device as recited in claim 13, wherein said means comprises:

means for determining said calibration factors using:

$$\begin{bmatrix} x_1 & y_1 & z_1 & 1 & -c_1x_1 & -c_1y_1 & -c_1z_1 \\ x_2 & y_2 & z_2 & 1 & -c_2x_2 & -c_2y_2 & -c_2z_2 \\ \vdots & \vdots & & \vdots & \vdots & & \\ \vdots & \vdots & & \vdots & \vdots & & \\ x_i & y_i & z_i & 1 & -c_ix_i & -c_iy_i & -c_iz_i \end{bmatrix}_{ix7} \begin{bmatrix} m_{11} \\ m_{12} \\ m_{13} \\ m_{14} \\ m_{31} \\ m_{32} \\ m_{33} \end{bmatrix}_{7x1} = \begin{bmatrix} c_1 \\ c_2 \\ c_3 \\ \vdots \\ \vdots \\ c_i \end{bmatrix}_{ix1} \text{ and}$$

$$\begin{bmatrix} x_1 & y_1 & z_1 & 1 & -l_1x_1 & -l_1y_1 & -l_1z_1 \\ x_2 & y_2 & z_2 & 1 & -l_2x_2 & -l_2y_2 & -l_2z_2 \\ \vdots & \vdots & & \vdots & \vdots & & \\ \vdots & \vdots & & \vdots & \vdots & & \\ x_i & y_i & z_i & 1 & -l_ix_i & -l_iy_i & -l_iz_i \end{bmatrix}_{ix7} \begin{bmatrix} m_{21} \\ m_{22} \\ m_{23} \\ m_{24} \\ m_{31} \\ m_{32} \\ m_{33} \end{bmatrix}_{7x1} = \begin{bmatrix} l_1 \\ l_2 \\ l_3 \\ \vdots \\ \vdots \\ l_i \end{bmatrix}_{ix1}$$

where $c_i$ is the column position and $l_i$ is the row position of an area element i, and $x_i$, $y_i$, and $z_i$ are respectively an x-coordinate, a y-coordinate, and a z-coordinate for an associated volume element i.

17. An image reconstruction device, comprising:

an x-ray source;

an x-ray detector disposed to face said source; and means for reconstructing said image from exposure data obtained from said detector by mapping a reconstructed image point from a known coordinate connected to said detector;

wherein said means comprises means for determining image coordinates $(c_i, l_i)$ of a reprojected point from a known position $(x_i, y_i, z_i)$ using:

$$c_i = \frac{m_{11}x_i + m_{12}y_i + m_{13}z_i + m_{14}}{m_{31}x_i + m_{32}y_i + m_{33}z_i + m_{34}}$$

$$l_i = \frac{m_{21}x_i + m_{22}y_i + m_{23}z_i + m_{24}}{m_{31}x_i + m_{32}y_i + m_{33}z_i + m_{34}}$$

where: m11, m12, . . . m34 are calibration factors.

18. A device as recited in claim 17, comprising:
means for determining said calibration factors using:

$$\begin{bmatrix} x_1 & y_1 & z_1 & 1 & 0 & 0 & 0 & 0 & -c_1x_1 & -c_1y_1 & -c_1z_1 \\ & \vdots & & & & \vdots & & & & \vdots & \vdots \\ 0 & 0 & 0 & 0 & x_1 & y_1 & z_1 & 1 & -l_1x_1 & -l_1y_1 & -l_1z_1 \\ & \vdots & & & & \vdots & & & & \vdots & \vdots \end{bmatrix}_{2N \times 11} \begin{bmatrix} m_{11} \\ m_{12} \\ m_{13} \\ m_{14} \\ m_{21} \\ m_{22} \\ m_{23} \\ m_{24} \\ m_{31} \\ m_{32} \\ m_{33} \end{bmatrix} = \begin{bmatrix} c_1 \\ c_2 \\ \vdots \\ \vdots \\ c_N \\ l_1 \\ \vdots \\ \vdots \\ l_N \end{bmatrix}_{2N \times 1}$$

where $c_i$ is the column position and $l_i$ is the row position of an area element i, and $x_i$, $y_i$, and $z_i$ are respectively an x-coordinate, a y-coordinate, and a z-coordinate for an associated volume element i.

* * * * *